US007795285B2

(12) United States Patent
Ihara et al.

(10) Patent No.: US 7,795,285 B2
(45) Date of Patent: Sep. 14, 2010

(54) ANTI-TRYPANOSOMIASIS AGENT

(75) Inventors: Masataka Ihara, c/o Hoshi University, 2-4-41, Ebara, Shinagawa-ku, Tokyo 142-8501 (JP); Kiyosei Takasu, Kyoto (JP); Khanitha Pudhom, Bangkok (TH); Hiroshi Kitaguchi, Minamiashigara (JP); Masayuki Kawakami, Minamiashigara (JP); Kozo Sato, Minamiashigara (JP)

(73) Assignees: Fujifilm Corporation, Tokyo (JP); Masataka Ihara, Sendai-shi (JP)

( * ) Notice: Subject to any disclaimer, the term of this patent is extended or adjusted under 35 U.S.C. 154(b) by 0 days.

(21) Appl. No.: 11/576,426

(22) PCT Filed: Sep. 29, 2005

(86) PCT No.: PCT/JP2005/017927

§ 371 (c)(1),
(2), (4) Date: Jun. 8, 2007

(87) PCT Pub. No.: WO2006/038513

PCT Pub. Date: Apr. 13, 2006

(65) Prior Publication Data

US 2008/0045574 A1    Feb. 21, 2008

(30) Foreign Application Priority Data

Oct. 4, 2004    (JP)    ............... 2004-291996

(51) Int. Cl.
*A01N 43/78*    (2006.01)
(52) U.S. Cl. .................................................. 514/369
(58) Field of Classification Search .................. 514/369
See application file for complete search history.

(56) References Cited

FOREIGN PATENT DOCUMENTS

| EP | 1623981 A1 | 2/2006 |
|---|---|---|
| JP | 2000-191531 | 7/2000 |
| JP | 2002-524524 | 6/2002 |
| JP | 2003-034640 | 2/2003 |
| JP | 2003-034641 | 2/2003 |
| JP | 2003-034642 | 2/2003 |
| JP | 2004-509083 | 3/2004 |
| JP | 2004-331545 | 11/2004 |
| WO | WO 02/17924 A1 | 3/2002 |

OTHER PUBLICATIONS

Howarth et al., "1,4-Dihydroxy-2,3-dioxatricyclo[8.4.0.0$^{4,9}$]tetradecane and Derivatives with In Vitro Activity Against *Plasmodium falciparum, Trypanasoma b brucei, Trypanasoma cruzi,* and *Leishmaniasis infantum*," Bioorganic & Medical Chemistry Letters, No. 13, 2013-2015 (2003).

Jones et al., "Analogues of Thiolactomycin as Potential Anti-Malarial and Anti-Trypanosomal Agents," *Bioorganic & Medical Chemistry*, No. 12, 683-692 (2004).
Takasu et al., "Antileishmanial Activities of Rhodacyanine Dyes," *Heterocycles*, vol. 64, 215-221, 2004.
Takasu et al., "Rhodacyanine Dyes as Antimalarials. 1. Preliminary Evaluation of Their Activity and Toxicity," *Journal of Medicinal Chemistry*, vol. 45, No. 5, 995-998, Feb. 28, 2002.
Published International Search Report for Application No. PCT/JP2005/017927.
English Translation of the International Preliminary Report on Patentability. Written opinion of the International Searching Authority in corresponding International Application No. PCT/JP2005/017927.
European Search Report completed on Jan. 13, 2010 and issued Jan. 26, 2010 for a corresponding European Counterpart Patent Appln. No. 05788281.3.
C. De Deigo et al., "Effect of heterocyclic analogues of triphenylmethane dyes against *Trypanosoma cruzi*", Annals of Tropical Medicine and Parasitology, (1988), vol. 82, No. 3, pp. 235-241.

*Primary Examiner*—Kamal A Saeed
*Assistant Examiner*—Valerie Rodriguez-Garcia
(74) *Attorney, Agent, or Firm*—Locke Lord Bissell & Liddell LLP

(57) ABSTRACT

The present invention is to provide an anti-trypanosomiasis agent having a high selective toxicity, and high preventing or treating effect against trypanosomiasis, comprising a compound shown by the following general formula (1) as an active ingredient

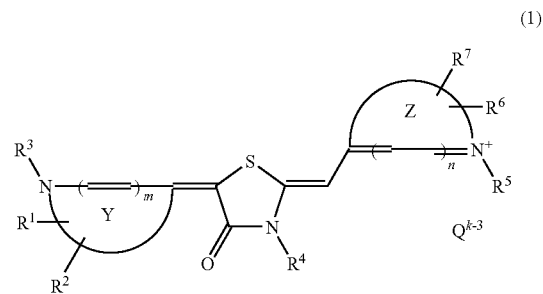

(1)

(wherein $R^1$ and $R^2$ each independently represents a hydrogen atom, halogen atom, hydroxyl group, oxygen atom, $C_{1-5}$ alkyl group, $C_{1-5}$ alkoxy group, $C_{5-8}$ aryl group, $C_{5-8}$ aryloxy group, $C_{2-6}$ alkoxycarbonyl group or $C_{2-6}$ alkylaminocarbonyl group, and may be bound to each other; $R^3$, $R^4$, and $R^5$ each independently represents a $C_{1-5}$ alkyl group or $C_{5-8}$ aryl group; $R^6$ and $R^7$ each independently represents a hydrogen atom, halogen atom, hydroxyl group, oxygen atom, $C_{1-8}$ alkyl group, $C_{1-5}$ alkoxy group, $C_{5-8}$ aryl group, $C_{5-8}$ aryloxy group, or $C_{2-6}$ alkoxycarbonyl group, and may be bound to each other; Y and Z each independently represents an atom group necessary to form a 5- or 6-membered heterocycle; m and n each represent 0 or 1; Q represents a physiologically acceptable anion; k represents an integer of 0 to 2, necessary to make the electric charge of the whole molecule 0).

4 Claims, No Drawings

ANTI-TRYPANOSOMIASIS AGENT

TECHNICAL FIELD

The present invention relates to a novel method for using rhodacyanine pigments, specifically to an anti-trypanosoma agent useful for preventing and treating effectively trypanosome infection, to which there is no effective treatment so far.

BACKGROUND ART

Trypanosomiasis which is induced by trypanosome protozoa is classified broadly into two groups, depending on the species of disease-causing parasites. The first group is African trypanosomiasis (African sleeping sickness) parasite of which is *Trypanosoma brucei*, which is further subdivided to *Trypanosoma brucei gambiense*, and *Trypanosoma brucei rhodesiense*. The second group is American trypanosomiasis (Chagas's disease) parasite of which is *Trypanosoma cruzi*. These protozoa infect not only human but various animals including dogs, cats, horses and cows. Therefore, it is concerned that infection of trypanosomiasis would be distributed around the world.

African trypanosomiasis-infected humans are observed throughout African continent, and it is estimated that there are approximately 60 millions of patients. Specifically, *Trypanosoma brucei gambiense* is observed in West and Central Africa, and *Trypanosoma brucei rhodesiense* is observed in East and South Africa. African trypanosomiasis is mediated by tsetse flies and is sometimes spread explosively where public hygiene is belated. Protozoa invades from the tsetse fly-bited site into blood flow or lymph nodes, inducing intermittent fever, headaches, ague, and transient edema. Later, when the central nervous system is invaded by protozoa, continuous headaches, somnolence during daylight, ataxio and coma appear, and finally leads the patient to death in several months to several years.

Agents for treating African trypanosomiasis are not satisfactory, and all of the agents require hospital admission and a long period administration. These agents are expensive, and often have harmful side-effects. For example, pentamidine which is used in the primary treatment is required to be administered at high doses by several intravenous or muscular injections within 3 weeks, which causes physical and economic burden. For central nervous systems diseases, melarsoprol, which is an agent containing arsenicum, is used. However, as it requires continuous administration for several weeks, side-effects lead by arsenic toxicity is inevitable. African trypanosomiasis is a life-threatening disease when left untreated, and development of a novel chemotherapeutic drug is awaited. Further, livestock including bovines and horses are infected by trypanosomiasis which result in death. Outbreaks often occur in Africa in livestock, which cause significant economic loss (for example, see Hoet, S. et al., Natural Product Reports, 2004, vol. 21, pp. 353-364).

Human infection of American trypanosomiasis (Shaga's disease) is reported mainly in many states in the United States, and throughout Central and South America. The total number of patients is roughly estimated to be approximately 20 millions. Mediating-insect of American trypanosomiasis is an insect relatively large called *Reduviidae*. When a person starches an itching site of a *Reduviidae*-bite, protozoa invade from *Reduviidae* feces and inoculate into blood flow or lymph nodes. Symptoms include fever, anthema, blepharedema, lymphadenitis, myocarditis, meningoencephalitis, and some cases are led to death within 2 to 4 weeks. Adults usually follow a chronic course, while children often exhibit acute symptoms and the fatality is said to be high. Benznidazole is used for treating American trypanosomiasis. However, it is only effective for early stage of infection, and requires to be administered continuously for 1 to 4 months. Further, carcinogenicity effect is reported. Therefore, as there is no effective drugs for American trypanosomiasis, World Health Organization (WHO) alerts that development of chemotherapeutic agents is necessary (for example, see Teixeira, M. M. et al., Trends Parasitology, 2002, vol. 18, pp. 262-268).

On the other hand, rhodacyanine pigments which are used in the present invention are known to be effective for treating tumors (for example, see Japanese Laid-Open Patent Application No. 5-117148). Further, the present inventors have proposed that rhodacyanine pigments show an anti-malarial activity (for example, see Japanese Laid-Open Patent Application No. 2000-191531; Japanese Laid-Open Patent Application No. 2003-034640; Japanese Laid-Open Patent Application No. 2003-034641; Japanese Laid-Open Patent Application No. 2003-034642).

Patent document 1: Japanese Laid-Open Patent Application No. 5-117148

Patent document 2: Japanese Laid-Open Patent Application No. 2000-191531

Patent document 3: Japanese Laid-Open Patent Application No. 2003-034640

Patent document 4: Japanese Laid-Open Patent Application No. 2003-034641

Patent document 5: Japanese Laid-Open Patent Application No. 2003-034642

Non-patent document 1: Hoet, S. et al., Natural Product Reports, 2004, vol. 21, pp. 353-364

Non-patent document 2: Teixeira, M. M. et al., Trends Parasitology, 2002, vol. 18, pp. 262-268

DISCLOSURE OF THE INVENTION

Object to be Solved by the Invention

The object of the present invention is to provide an anti-trypanosomiasis agent having a high selective toxicity and a superior treating or preventing effect against Trypanosomiasis including African trypanosomiasis and American trypanosomiasis.

Means to Solve the Object

In order to solve the above object, the present inventors synthesized a number of compounds, and conducted a number of pharmacological activity test with the growth inhibition effect of *Trypanosoma* protozoa as an index. They found out that rhodacyanine pigments show a potent growth inhibition activity against trypanosomiasis, and have a significant low toxicity against mammal cells, which is an index of side-effects. Thus, they completed the present invention.

In other words, the present invention relates to ("1") an anti-trypanosomiasis agent comprising a compound shown by the following general formula (1) as an active ingredient

[Chemical Formula 1]

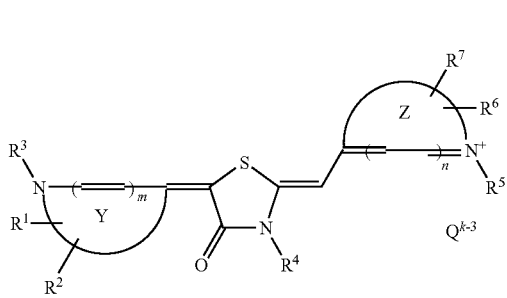

(wherein $R^1$ and $R^2$ each independently represents a hydrogen atom, halogen atom, hydroxyl group, oxygen atom, $C_{1-5}$ alkyl group, $C_{1-5}$ alkoxy group, $C_{5-8}$ aryl group, $C_{5-8}$ aryloxy group, $C_{2-6}$ alkoxycarbonyl group or $C_{2-6}$ alkylaminocarbonyl group, and may be bound to each other; $R^3$, $R^4$, and $R^5$ each independently represents a $C_{1-5}$ alkyl group or $C_{5-8}$ aryl group; $R^6$ and $R^7$ each independently represents a hydrogen atom, halogen atom, hydroxyl group, oxygen atom, $C_{1-8}$ alkyl group, $C_{1-5}$ alkoxy group, $C_{5-8}$ aryl group, $C_{5-8}$ aryloxy group, or $C_{2-6}$ alkoxycarbonyl group, and may be bound to each other; Y and Z each independently represents an atom group necessary to form a 5- or 6-membered heterocycle; m and n each represents 0 or 1; Q represents a physiologically acceptable anion; k represents an integer of 0 to 2, necessary to make the electric charge of the whole molecule 0).

Moreover, the present invention relates to ("2") the anti-trypanosomiasis agent according to "1", wherein the compound shown by general formula (1) is a compound shown by the following general formula (2)

[Chemical Formula 2]

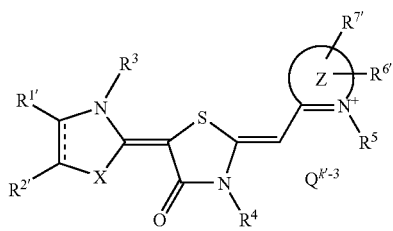

(wherein $R^{1'}$ and $R^{2'}$ each independently represents a hydrogen atom, $C_{1-5}$ alkyl group, or $C_{5-8}$ aryl group, and may be bound to each other; $R^{6'}$ and $R^{7'}$ each independently represents an hydrogen atom, halogen atom, hydroxyl group, oxygen atom, $C_{1-8}$ alkyl group, $C_{1-5}$ alkoxy group, or $C_{5-8}$ aryl group, and may be bound to each other; X represents a sulfur atom or oxygen atom; k' represents 1 or 2, necessary to make the electric charge of the whole molecule 0).

Moreover, the present invention relates to ("3") the anti-trypanosomiasis agent according to "1", wherein the compound shown by general formula (1) is a compound shown by the following general formula (3)

[Chemical Formula 3]

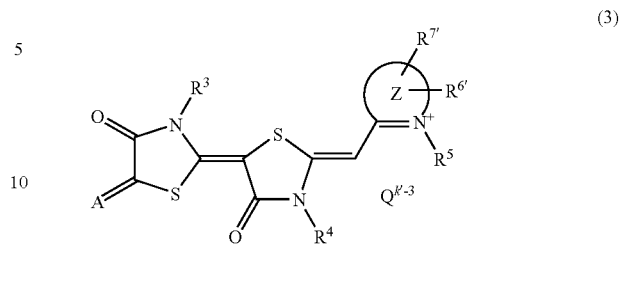

(wherein $R^{6'}$ and $R^{7'}$ each independently represents an hydrogen atom, halogen atom, hydroxyl group, oxygen atom, $C_{1-8}$ alkyl group, $C_{1-5}$ alkoxy group, or $C_{5-8}$ aryl group, and may be bound to each other; A represents a 5- or 6-membered heterocycle, or a condensation ring wherein 1 or more 3- to 8-membered ring is condensed thereto; k' represents 1 or 2, necessary to make the electric charge of the whole molecule 0); and ("4") the anti-trypanosomiasis agent according to any one of "1" to "3", wherein Q represents a halogen ion, sulphonate ion, or carboxylate ion.

BEST MODE OF CARRYING OUT THE INVENTION

An anti-trypanosomiasis agent of the present invention is not particularly limited as long as it is a medicinal composition comprising a compound shown by the following general formula (1) as an active ingredient, and it can contain one or more kind of compound shown by general formula (1). Usually, the compound is contained together with a pharmaceutically acceptable carrier or diluent.

[Chemical Formula 4]

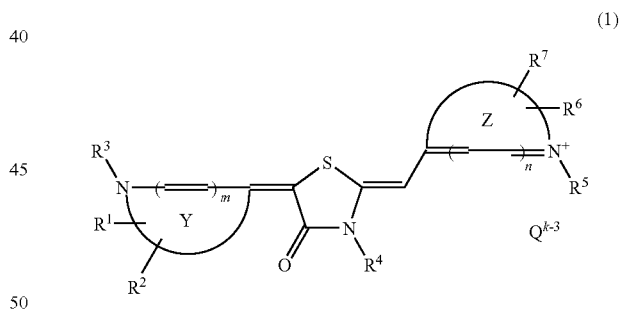

In general formula (1), $R^1$ and $R^2$ each independently represents a hydrogen atom, halogen atom, hydroxyl group, oxygen atom, $C_{1-5}$ alkyl group, $C_{1-5}$ alkoxy group, $C_{5-8}$ aryl group, $C_{5-8}$ aryloxy group, $C_{2-6}$ alkoxycarbonyl group or $C_{2-6}$ alkylaminocarbonyl group.

Examples of halogen atoms represented by $R^1$ and $R^2$ in general formula (1) include chlorine, bromine, fluorine, and iodine.

A $C_{1-5}$ alkyl group represented by $R^1$ and $R^2$ in general formula (1) may be in a linear form, branched form or cyclic form. The alkyl group may be substituted, and preferred substituents include an alkyl group with 1 to 5 carbons, alkenyl group with 2 to 5 carbons, alkynyl group with 2 to 5 carbons, alkoxy group with 1 to 5 carbons, aryloxy group with 6 to 8 atoms, halogen atoms (chlorine, bromine, fluorine, iodine, etc), aryl group with 6 to 8 carbons, hydroxyl group, amino group, amino group substituted with alkyl group or aryl group, acylamino group, sulphonylamino group, carbamoyl group, sulfamoyl group, carboxyl group, alkoxycarbonyl group with 2 to 5 carbons, acyloxy group with 2 to 5 carbons, 5- or 6-membered heterocycle (pyrrole ring, furan ring, piperidine ring, morpholine ring, pyridinering, etc.), cyano group, and nitro group. These substituents may be further substituted by each other. Specific alkyl group represented by R1 and R2 include a methyl group, ethyl group, hydroxyethyl group, 2-propenyl group, benzyl group, propyl group, and butyl group.

A $C_{1-5}$ alkoxy group represented by $R^1$ and $R^2$ in general formula (1) may be in a linear form, or in a branched form. Moreover, it may be substituted, and as substituents, the same as those for the above alkyl group can be exemplified. Specific alkoxy group represented by $R^1$ and $R^2$ include methoxy group, ethoxy group, hydroxyethoxy group, 2-propenyloxy group, benzyloxy group, propoxy group and butoxy group.

A $C_{5-8}$ aryl group represented by $R^1$ and $R^2$ in general formula (1) may be substituted, and as substituents, the same as for the above alkyl group can be exemplified. Specific examples of $C_{5-8}$ aryl group represented by $R^1$ and $R^2$ include phenyl group, tryl group, p-chlorophenyl group.

A $C_{5-8}$ aryloxy group represented by $R^1$ and $R^2$ in general formula (1) may be substituted, and as substituents, the same as those for the above alkyl group can be exemplified. Specific examples of $C_{5-8}$ aryloxy group represented by $R^1$ and $R^2$ include phenoxy group, tolyloxy group, p-chlorophenoxy group.

A $C_{2-6}$ alkoxycarbonyl group represented by $R^1$ and $R^2$ in general formula (1) may be substituted, and as substituents, the same as those for the above alkyl group can be exemplified. Specific examples of $C_{2-6}$ alkoxycarbonyl group represented by R1 and R2 include methoxycarbonyl group and ethoxycarbonyl group.

A $C_{2-6}$ alkylaminocarbonyl group represented by $R^1$ and $R^2$ in general formula (1) may be substituted, and as substituents, the same as those for the above alkyl group can be exemplified. Specific examples of $C_{2-6}$ alkylaminocarbonyl group represented by $R^1$ and $R^2$ include aminomethylcarbonyl group and aminoethylcarbonyl group.

The above $R^1$ and $R^2$ may be bound to each other, and can form, for example, 1 or more 3- to 8-membered ring. Specifically, it can form a benzene ring, naphthalene ring, etc.

In general formula (1), $R^3$, $R^4$, and $R^5$ each independently represents a $C_{1-5}$ alkyl group or $C_{5-8}$ aryl group, and are the same as those represented by $R^1$ and $R^2$ in general formula (1), respectively.

In general formula (1), $R^6$ and $R^7$ each independently represents a hydrogen atom, halogen atom, hydroxyl group, oxygen atom, $C_{1-8}$ alkyl group, $C_{1-5}$ alkoxy group, $C_{5-8}$ aryl group, $C_{5-8}$ aryloxy group, or $C_{2-6}$ alkoxycarbonyl group, and are the same as those represented by $R^1$ and $R^2$ in general formula (1). Further, similarly as $R^1$ and $R^2$, they may be bound to each other, and can form, for example 1 or more 3- to 8-membered ring. Specifically, they can form a benzene ring, naphthalene ring, etc.

In general formula (1), Y and Z each independently represents an atom group necessary to form a 5- or 6-membered heterocycle.

A 5- or 6-membered heterocycle formed by Y and Z in general formula (1) may be a saturated ring or unsaturated ring. Examples of hetero atoms included in the heterocycle include a nitrogen atom, oxygen atom, sulfur atom, selenium atom, tellurium atom, silicon atom, and phosphorus atom. Y and Z may have 1 or more substituents, and the substituents are the same as for the above alkyl group represented by $R^1$ and $R^2$ in general formula (1).

Specific examples of 5- or 6-membered heterocycle formed by Y and Z include: thiazole ring (for example, thiazole, 4-methylthiazole, 4-phenylthiazole, 4,5-diphenylthiazole, 4,5-dimethylthiazole, etc.), benzothiazole ring (for example, benzothiazole, 5-methylbenzothiazole, 5-phenylbenzothiazole, 5-metoxybenzothiazole, 4-fluorobenzothiazole, 5,6-dioxymethylenebenzothiazole, 5-nitrobenzothiazole, 5-trifluoromethylbenzothiazole, 5-metoxycarbonylbenzothiazole, 6-hydroxybenzothiazole, 5-cyanobenzothiazole, 5-iodobenzothiazole, etc.), naphtothizaole ring (for example, α-naphtothiazole, β-naphtothiazole, γ-naphtothiazole, 5-methoxy-β-naphtothiazole, 8-methoxy-α-naphtothiazole, 6-methoxy-8-acetoxy-β-naphtothiazole, 8,9-dihydroxy-β-nathtothiazole, etc.), oxazole ring (for example, 4-methyloxazole, 4-phenyloxazole, 4,5-diphenyloxazole, 4-phenoxyoxazole, etc.) benzoxazole ring (for example, benzoxazole, 5-chlorobenzoxazole, 5,6-dimethylbenzoxazole, 6-hydroxybenzoxazole, 5-phenylbenzoxazole, etc.), naphtoxazole ring (for example, α-naphtoxazole, β-naphtoxazole, γ-naphtoxazole, etc.), selenazole ring (for example, 4-methylselenazole, 4-phenylselenazole, etc.), benzselenazole ring (for example, benzselenazole, 5-chlorobenzselenazole, 5,6-dimethylbenzselenazole, 6-hydroxybenzselenazole, 5-phenylbenzselenazole, etc.), thiazoline ring (for example, thiazoline, 4,4-dimethylthiazoline, etc.), 2-pyridine ring (for example, 2-pyridine, 5-methyl-2-pyridine, 5-methoxy-2-pyridine, 4-chloro-2-pyridine, 5-carbamoyl-2-pyridine, 5-methoxycarbonyl-2-pyridine, 4-acetylamino-2-pyridine, 6-methylthio-2-pyridine, 6-methyl-2-pyridine, etc.), 4-pyridine ring (for example, 4-pyridine, 3-methoxy-4-pyridine, 3,5-dimethyl-4-pyridine, 3-chloro-4-pyridine, 3-methyl-4-pyridine, etc.), 2-quinoline ring (for example, 2-quinoline, 6-methyl-3-quinoline, 6-chloro-2-quinoline, 6-ethoxy-2-quinoline, 6-hydroxy-2-quinoline, 6-nitro-2-quinoline, 6-acetylamino-2-quinoline, 8-fluoro-2-quinoline, etc.), 4-quinoline ring (for example, 4-quinoline, 6-methoxy-4-quinoline, 6-acetylamino-4-quinoline, 8-chloro-4-quinoline, 8-trifluoromethyl-4-quinoline, etc.), 1-isoquinoline ring (for example, 1-isoquinoline, 6-methoxy-1-isoquinoline, 6-acetylamino-1-isoquinoline, 6-chloro-1-isoquinoline, etc.), 3,3-dialkylindolenine ring (for example, 3,3-dimethylindolenine, 3,3,7-trimethylindolenine, 5-chloro-3,3-dimethylindolenine, 5-ethoxycarbonyl-3,3-dimethylindolenine, 5-nitro-3,3-dimethylindolenine, 3,3-dimethyl-4,5-phenyleneindolenine, 3,3-dimethyl-6,7-phenyleneindolenine, 5-acetylamino-3,3-diethylindolenine, 5-diethylamino-3,3-dipropylindolenine, 5-benzoylamino-3-ethyl-3-methylindolenine, etc.), imidazole ring (for example, imidazole, 1-methyl-4-phenylimidazole, 1-benzyl-4,5-dimethylimidazole, etc.), benzimidazole ring (for example, benzimidazole, 1-methylbenzimidazole, 1-methyl-5-trifluoromethylbenzimidazole, 1-ethyl-5-chlorobenzimidazole, 1-phenyl-5-methoxycarbonylbenzimidazole, 1-ethyl-5-dimethylaminobenzimidazole, etc.), naphtoimidazole ring (for example, 1-methyl-α-naphtoimidazole, 1-methyl-5-methoxy-β-naphtoimidazole, etc.).

In general formula (1), Q represents a physiologically acceptable anion. Such physiologically acceptable anion relates to an ion that is nontoxic when a compound shown by general formula (1) is administered to a recipient, and that dissolves the compound shown by general formula (1) to an aqueous system. Examples of physiologically acceptable anion represented by Q include: halogen ions such as chlorine ion, bromine ion, iodine ion; sulfonate ions such as aliphatic and aromatic sulfonate ion including methanesulfonate ion, trifluoromethanesulfonate ion, p-toluenesulfonate ion, naphthalenesulfonate ion, 2-hydroxyethanesulfonate ion; sulfamate ion such as cyclohexanesulfamate ion; sulfate ion such as methylsulfate ion and ethylsulfate ion; hydrogen sulfate ion; borate ion; alkyl and dialkyl phosphate ions such as diethylphosphate ion and methyl hydrogen phosphate ion; pyrophosphate ion such as trimethylpyrophosphate ion; carbonate ion (carbonate ion wherein carboxy group and hydroxyl group are substituted is suitably used); carbonate ion; hydrogencarbonate ion and hydroxide ion; acetate ion; propionate ion; valerate ion; citrate ion; maleate ion; fumarate ion; lactate ion; succinate ion; tartrate ion; benzoate ion. Halogen ion, sulfonate ion or carboxylate ion is preferred.

In general formula (1), m and n each represents 0 or 1, and k represents an integer of 0 to 2 necessary to make the electric charge of the whole molecule 0.

Further, a compound shown by general formula (1) is preferably a compound shown by the following general formula (2) or the following general formula (3).

[Chemical Formula 5]

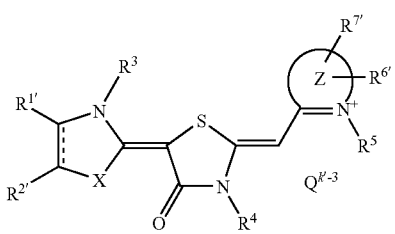

(2)

In general formula (2), $R^{1'}$ and $R^{2'}$ each independently represents a hydrogen atom, $C_{1-5}$ alkyl group, or $C_{5-8}$ aryl group, and are the same as those represented by $R^1$ and $R^2$ in general formula (1). Further $R^{1'}$ and $R^{2'}$ may be bound to each other, and can form, for example 1 or more 3- to 8-membered ring. Specifically, they can form a benzene ring, naphthalene ring, etc.

In general formula (2), $R^{6'}$ and $R^{7'}$ each independently represents a hydrogen atom, halogen atom, hydroxyl group, oxygen atom, $C_{1-8}$ alkyl group, $C_{1-5}$ alkoxy group, or $C_{5-8}$ aryl group, and are the same as those represented by $R^6$ and $R^7$ in general formula (1), respectively. Further $R^6$ and $R^7$ may be bound to each other, and can form, for example 1 or more 3- to 8-membered ring. Specifically, they can form a benzene ring, naphthalene ring, etc.

In general formula (2), X represents a sulfur atom or oxygen atom. In general formula (2), k' represents 1 or 2, necessary to make the electric charge of the whole molecule 0.

[Chemical Formula 6]

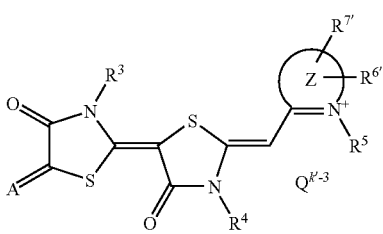

(3)

In general formula (3), $R^{6'}$ and $R^{7'}$ each independently represents a hydrogen atom, halogen atom, hydroxyl group, oxygen atom, $C_{1-8}$ alkyl group, $C_{1-5}$ alkoxy group, or $C_{5-8}$ aryl group, and are the same as those represented by $R^6$ and $R^7$ in general formula (1), respectively. Further $R^{6'}$ and $R^{7'}$ may be bound to each other, and can form, for example 1 or more 3- to 8-membered ring. Specifically, they can form a benzene ring, naphthalene ring, etc.

In general formula (3), A represents a 5- or 6-membered heterocycle, or a condensation ring wherein 1 or more 3- to 8-membered ring is condensed thereto. The 5- or 6-membered heterocyle is the same as those represented by Y and Z of general formula (1). Further, a 3- to 8-membered ring in the condensation ring to which 1 or more 3- or 8-membered ring is condensed to the above 5- or 6-membered ring may be a saturated ring or unsaturated ring. Specific examples include cyclopropane ring, cyclopropene ring, cyclobutane ring, cyclobutene ring, cyclopentane ring, cyclopentene ring, cyclohexane ring, cyclohexene ring, cycloheptane ring, cycloheptene ring, cyclooctane ring, cyclooctene ring, benzene ring, naphthalene ring, anthracene ring, phenanthrene ring, thiophene ring, pyridine ring. Among these, a 5- or 6-membered ring is particularly preferred. Further, A may have 1 or 2 or more substituents, and as substituents, similar ones as for the alkyl group represented by $R^1$ and $R^2$ in general formula (1) can be exemplified.

In general formula (2), k' represents 1 or 2, necessary to make the electric charge of the whole molecule 0.

Compounds shown by the general formulae (1) to (3) of the present invention can be easily manufactured from known starting materials, according to methods disclosed in Japanese Laid-Open Patent Application No. 5-117148, Japanese Laid-Open Patent Application No. 2000-191531, Japanese Laid-Open Patent Application No. 2003-034640, Japanese Laid-Open Patent Application No. 2003-034641, Japanese Laid-Open Patent Application No. 2003-034642, Japanese Laid-Open Patent Application No. 2003-128454; Takasu, K, et al., Journal of Medicinal Chemistry, 2002, vol. 45, pp. 995-998; Takasu, K, et al., Journal of Combinatorial Chemistry, 2003, vol. 5, pp. 211-214.

Typical examples of compounds shown by general formulae (1) to (3) include the following compounds, while it is not limited to these compounds.

[Chemical Formula 7]

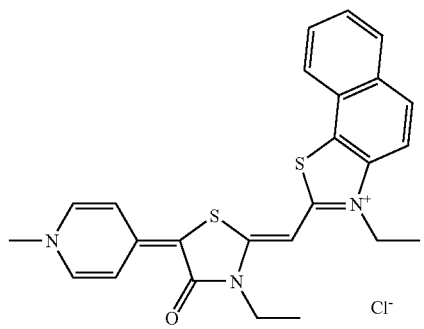

A-1

-continued
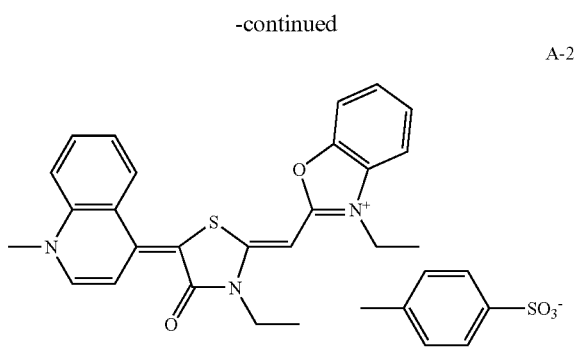
A-2
[Chemical Formula 8]
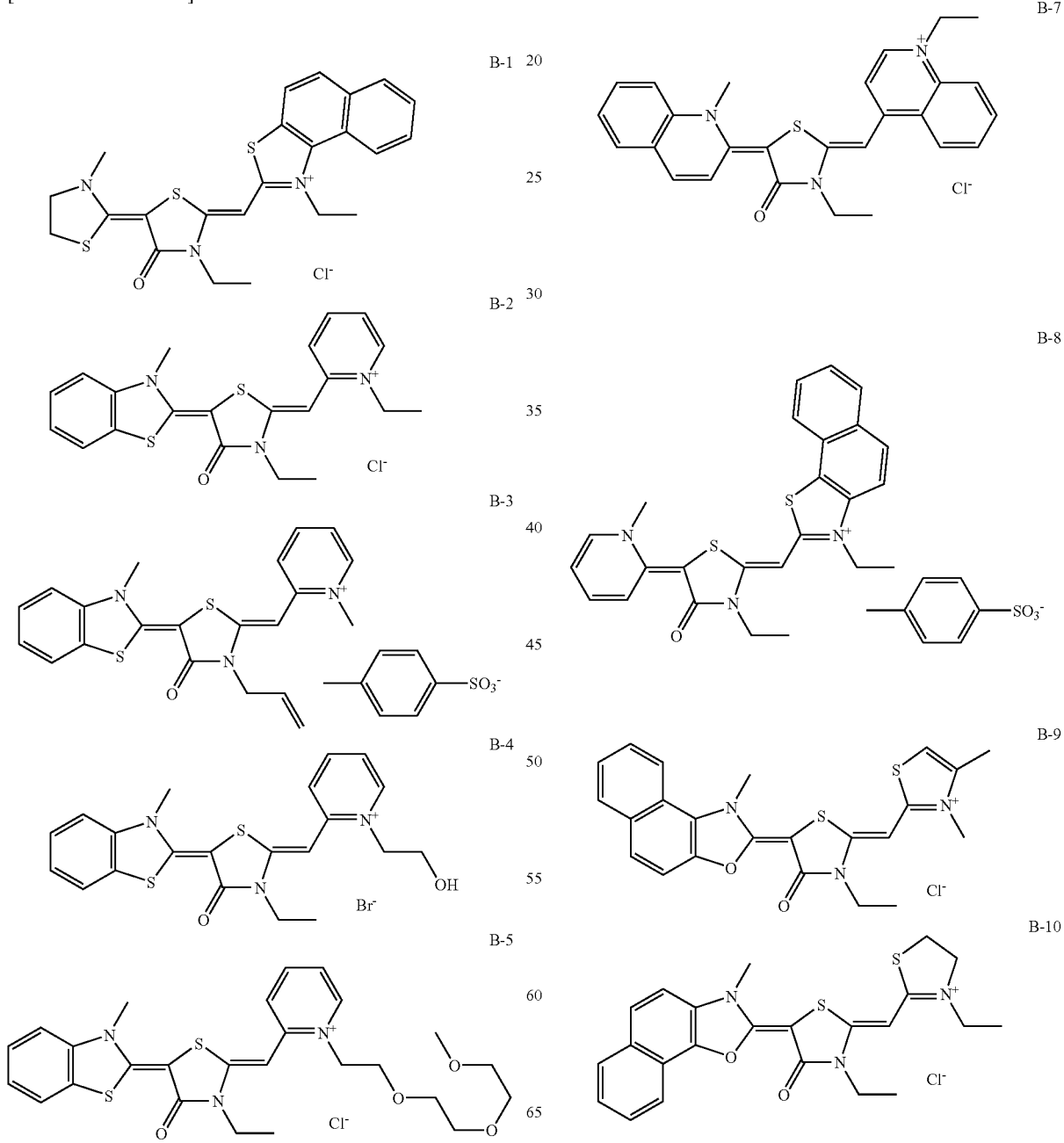
-continued
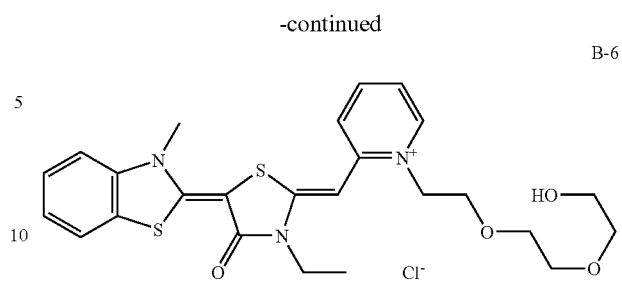
B-6
[Chemical Formula 9]

[Chemical Formula 10]

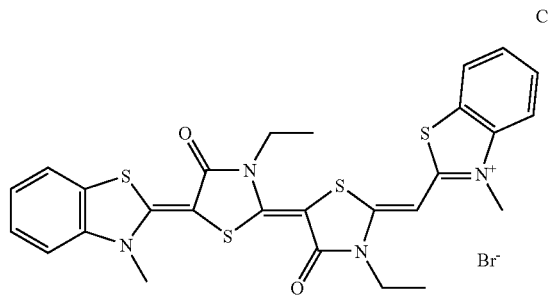

An anti-trypanosomiasis agent of the present invention may be used effectively for preventing or treating trypanosomiasis including African trypanosomiasis and American trypanosomiasis. An anti-trypanosomiasis agent of the present invention may contain a conventionally used anti-trypanosomiasis agent, according to need. Suitable examples of such conventionally used anti-trypanosomiasis agent include pentamidine, melarsoprol and benznidazole.

Moreover, as medicinal carriers or diluents that can be used with the compounds shown by general formulae (1) to (3) of the present invention, medicinal carriers or diluents that are commonly used conventionally may be used, and examples include the following: glucose; saccharose; lactose; ethyl alcohol; glycerol; mannitol; sorbitol; pentaerythritol; diethylene glycol; propylene glycol, dipropylene glycol, polyethylene glycol 400, other polyethylene glycol; mono-, di- and tri-glyceride of fatty acids including trilaurate glyceryl and distearate glyceryl; pectin; starch; arginine acid; xylose; talc; lycopodium; olive oil; oil and fat including peanut oil, castor oil, corn oil, safflower oil, wheat germ oil, sesame oil, cotton seed oil, sunflower oil and oleum morrhuae; gelatin; lecithin; silica; cellulose; cellulose derivatives including methylhydroxypropyl cellulose, methyl cellulose and hydroxyethyl cellulose; salts of fatty acids with 12 to 22 carbon atoms including calcium stearate, calcium laurate, magnesium oleate, calcium palminate, calcium behenate and magnesium stearate; cyclodextrins (for example, α-cyclodextrin, β-cyclodextrin, γ-cyclodextrin, hydroxyethyl-β-cyclodextrin, hydroxypropyl-β-cyclodextrin, dihydroxypropyl-β-cyclodextrin, carboxymethylethyl-β-cyclodextrin, cycloawaodorin, and dimethyl-β-cyclodextrin, etc.); emulsifier (for example, ester of saturated and unsaturated fatty acids with 2 to 22, particularly 10 to 18 carbon atoms, with monovalent aliphatic alcohol or polyvalent alcohol with 1 to 20 carbon atoms including glycerol, glycerine, diethylene glycol, pentaerythritol, ethyl alcohol and butyl alcohol, octadecyl alcohol); and silicone such as dimethylpolysiloxane.

Further, pharmaceutically effective dose and administration method or administration means of the compound shown by general formulae (1) to (3) of the present invention depend on types of parasitic protozoa being the cause of the infection, habitats of protozoa, seriousness of diseases, treatment strategies, age, body weight, sex, and general health conditions of the patient, and (genetic) racial background of the patient. However, generally, the dosage of the present invention is 1 to 2000 mg, more generally 50 to 500 mg/day/70 kg of body weight. Suitable administration method include, for example, injecting intravenously, intraperitoneally, or subcutaneously as diluted to 5% glucose aqueous solution, or in a form accompanied with the above carrier or diluent; administrating orally; or applying to skin.

In order to clarify the effectivity of the compound shown by general formulae (1) to (3) of the present invention and its medicinal composition, Examples will be shown in the following, while the technical scope of the present invention will not be limited to these exemplifications.

Example 1

1-1. Culture of African *Trypanosoma* Protozoa

In the present example, protozoa of *Trypanosoma brucei rhodensiense* (STIB 900 strain), a trypamastigote living in blood stream, was used. The medium used in the experiment was a MEM medium which was sterilized with a filter and supplemented with 25 mM N-2-hydroxyethylpiperazine-2-ethansulfonic acid (HEPES), 1 g/L glucose, 1% MEM non-essential amino acid, 0.2 mM 2-mercaptoethanol, 2 mM sodium pyruvate, 0.1 mM hypoxanthine, and 15% heat-treated horse serum. The protozoa was cultured in an atmosphere of $CO_2$ concentration 5%, at a temperature of 37° C.

1-2. African Trypanosome Protozoa Growth Inhibition Screening Test

The compounds of the present invention to be used in the present test and the positive target drug (melarsoprol) were dissolved in DMSO to make a test solution of a predetermined concentration. A medium containing $8 \times 10^3$ protozoa, and a test solution containing a drug of a predetermined concentration or a drug-free DMSO were added to wells of a 96-well culture plate, and subsequently, medium was added so that the amount in each well becomes 100 μL. Test solutions were taken by duplicates. After culturing the culture plate for 72 hours in an incubator, growth inhibition activity was tested. Test was conducted as follows.

10 μL of Alamar Blue aqueous solution was added to each well, and the resultant was further cultured for 2 hours. Next, the culture plate was placed on a fluorescent micro-plate reader (Spectramax Gemeni XS; US Molecular Device), radiated at an excited wavelength of 536 nm. Fluorescent intensity was measured at 588 nm, to calculate the trypanosome protozoa infected rate of the test solution added-group, and of the control group. From the protozoan infection rate obtained in the above, growth inhibition rate was calculated with the following formula, to obtain a 50% growth inhibition concentration ($IC_{50}$).

Growth inhibition rate (%)={1−(b−a)/(c−a)}×100 a: early infection rate b: infection rate when test solution was added c: infection rate of the control 1-3. Growth Inhibition Test of Rat L6 Cells Rat derived-L6 cells (rat skeletal myoblast cell) were used. As medium, RPMI1640 medium was supplemented so that L-glutamin (200 mM) is 1%, and fetal bovine serum 10%, and the medium was cultured under $CO_2$ concentration 5%, at 37° C. The compounds of the present invention and the target drugs to be used in the test were dissolved in DMSO, to make a test solution of a predetermined concentration. Pre-culture was conducted and medium containing cells which have entered the logarithmic growth phase was taken to wells of a 96-well culture plate. Then, a test solution containing drug of a predetermined concentration or a drug-free DMSO was added. Test solutions were taken by duplicates. Culture plate was cultured for 72 hours in an incubator, to test the growth inhibition activity. Test was conducted as follows.

10 μL of Alamar Blue aqueous solution was added to each well, and the resultant was further cultured for 2 hours. Next, the culture plate was placed on a fluorescent micro-plate reader (Spectramax Gemeni XS; US Molecular Device), radiated at an excited wavelength of 536 nm. Fluorescent intensity was measured at 588 nm, and residual rate of L6 cells of the test solution added group, and that of the control was calculated. From the cell residual rate obtained in the above, growth inhibition rate to L6 cells was calculated, to obtain a 50% growth inhibition concentration ($IC_{50}$).

Growth inhibition rate (%)={(C-A)/(B-A)}×100

A: primary cell count

B: cell count of control 3 days after

C: cell count of wells added with a sample, 3 days after

1-4. Determination of Drug Efficacy of African Trypanosome

Chemotherapy index used as an index of selective toxicity against African trypanosome protozoa was calculated with the following formula, to determine drug efficacy.

Chemotherapy index = ($IC_{50}$ value of a sample against rat L6 cells)/

($IC_{50}$ value of a sample against African trypanosome protozoa)

$IC_{50}$ values of samples of the compounds of the present invention and the positive target drug against African trypanosome protozoa and rat L6 cells, as well as selective toxicity index are shown in Table 1.

TABLE 1

| compounds | 50% growth inhibiting concentration (μM) | | Selective toxicity |
|---|---|---|---|
| | *Trypanosoma brucei* rhod. | Cytotoxicity L6 | |
| A-1 | 0.76 | 134 | 176 |
| A-2 | 0.012 | 6.4 | 533 |
| B-1 | 0.095 | 193 | 2030 |
| B-2 | 0.49 | 115 | 235 |
| B-3 | 0.41 | 105 | 256 |
| B-4 | 1.9 | 180 | 95 |
| B-5 | 0.37 | 125 | 338 |
| B-6 | 0.94 | 61.9 | 66 |
| B-7 | 0.041 | 6.0 | 146 |
| B-8 | 0.10 | 25.2 | 252 |
| B-9 | 0.024 | 14.2 | 592 |
| B-10 | 0.035 | 18.5 | 529 |
| C-1 | 0.009 | >140 | >15600 |
| melarsoprol | 0.006 | 7.8 | 1300 |

The compounds of the present invention showed a similar or superior growth inhibiting effect as the existing drug, melarsoprol. Moreover, they did not show weak toxicity against normal cells.

Example 2

2-1. Culture of American *Trypanosoma* Protozoa

In the present example, amastigote and trypomastigote infected with rat L6 cells of protozoa of *Trypanosoma cruzi* (Tulahuen C2C4 strain) were used. As medium used in the test, RPMI 1640 medium containing L6 cells was supplemented so that L-glutamine (200 mM) becomes 1%, fetal bovine serum becomes 10%, which was cultured under $CO_2$ concentration 5%, at 37° C.

2-2. American Trypanosome Protozoa Growth Inhibition Screening Test

The compounds of the present invention to be used in the test and the positive target agent (benznidazole) were dissolved in DMSO to make a test solution of a predetermined concentration. A medium containing $5\times10^3$ protozoa was added to wells of a 96-well culture plate, and pre-cultured for 48 hours. After replacing the medium, test solution containing drug of a predetermined concentration or a drug-free DMSO was added. Test solutions were taken by duplicates. After culturing the culture plate in an incubator for 96 hours, growth inhibition activity was tested. Test was conducted as follows.

50 μL of CPRG/Nonidet was added to each well, and allowed to rest for 2 to 6 hours. Next, the culture plate was placed on a fluorescent micro-plate reader, and the absorbance was measured at 540 nm. Growth inhibition rate was calculated with the following formula based on the protozoan infection rate which was obtained by calculating trypanosome infection rate of test solution added group and control group, to obtain a 50% growth inhibition concentration ($IC_{50}$).

Growth inhibition rate (%)={1-(b-a)/(c-a)}×100 a: early infection rate b: infection rate when test solution was added c: infection rate of the control

2-3. Determination of Drug Efficacy of American Trypanosome

Chemotherapy index used as an index of selective toxicity against American trypanosome protozoa was calculated with the following formula, to determine drug efficacy.

Chemotherapy index = ($IC_{50}$ value of a sample against rat L6 cells)/

($IC_{50}$ value of a sample against American trypanosome protozoa)

$IC_{50}$ values of samples of the compounds of the present invention and the positive target drug against American trypanosome protozoa and rat L6 cells, as well as selective toxicity index are shown in Table 2.

TABLE 2

| compounds | 50% growth inhibiting concentration (μM) | | Selective toxicity |
|---|---|---|---|
| | *Trypanosoma cruzi* | Cytotoxicity L6 | |
| A-1 | 48 | 134 | 2.8 |
| A-2 | 0.53 | 6.4 | 10 |
| B-1 | 40 | 193 | 4.8 |
| B-2 | 6.8 | 115 | 17 |
| B-3 | 4.3 | 105 | 24 |
| B-5 | 29 | 125 | 4.3 |
| B-7 | 0.43 | 6.0 | 12 |

TABLE 2-continued

| compounds | 50% growth inhibiting concentration (μM) | | Selective toxicity |
|---|---|---|---|
| | Trypanosoma cruzi | Cytotoxicity L6 | |
| B-8 | 1.8 | 25.3 | 14 |
| B-9 | 0.22 | 14.2 | 65 |
| B-10 | 0.35 | 18.5 | 53 |
| C-1 | 14 | >140 | >10 |
| benznidazole | 0.87 | — | — |

The compounds of the present invention showed a similar or superior growth inhibiting effect as the existing drug, benznidasol. Moreover, they did not show a potent toxicity against normal cells.

From the results of Examples 1 and 2, it has been clarified that the compounds of the present invention show a growth inhibition effect against African trypanosomiasis protozoa and American trypanosomiasis protozoa even when a low dosage is administered, and that the compounds do not damage mammal cells compared to protozoa does, even when administrated at a high dosage. In other words, form the above results, it has been clarified that the compounds of the present invention are suitable as drugs preventing or treating trypanosomiasis including African trypanosomiasis and American trypanosomiasis.

INDUSTRIAL APPLICABILITY

According to the present invention, a preventative or therapeutic composition against trypanosomiasis including African trypanosomiasis and American trypanosomiasis can be provided.

The invention claimed is:

1. A method of treating trypanosomiasis comprising administering an effective amount of an anti-trypanosomiasis agent comprising a compound of the following formula (1) as an active ingredient

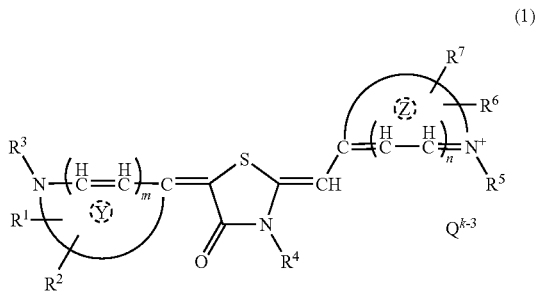

(1)

wherein $R^1$ and $R^2$ each independently represents a hydrogen atom, halogen atom, hydroxyl group, oxygen atom, $C_{1-5}$ alkyl group, $C_{1-5}$ alkoxy group, $C_{5-8}$ aryl group, $C_{5-8}$ aryloxy group, $C_{2-6}$ alkoxycarbonyl group or $C_{2-6}$ alkylaminocarbonyl group, and may be bound to each other; $R^3$, $R^4$, and $R^5$ each independently represents a $C_{1-5}$ alkyl group or $C_{5-8}$ aryl group; $R^6$ and $R^7$ each independently represents a hydrogen atom, halogen atom, hydroxyl group, oxygen atom, $C_{1-8}$ alkyl group, $C_{1-5}$ alkoxy group, $C_{5-8}$ aryl group, $C_{5-8}$ aryloxy group, or $C_{2-6}$ alkoxycarbonyl group, and may be bound to each other; Y and Z each independently represents a 5- or 6-membered heterocycle together with the nitrogen atom, in which hetero atoms included in the heterocyle include a nitrogen atom, oxygen atom, sulfur atom, selenium atom, tellurium atom, silicon atom, and phosphorus atom; m and n each represents 0 or 1; Q represents a physiologically acceptable anion; k represents an integer of 0 to 2, necessary to make the electric charge of the whole molecule 0.

2. The method of treating trypanosomiasis comprising administering the anti-trypanosomiasis agent according to claim 1, wherein the compound of formula (1) is a compound of the following formula (2)

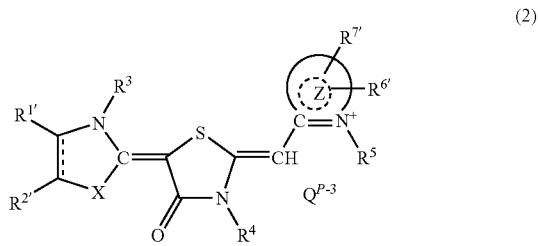

(2)

wherein ------ represents a single bond or double bond; $R^{1'}$ and $R^{2'}$ each independently represents a hydrogen atom, $C_{1-5}$ alkyl group, or $C_{5-8}$ aryl group, and may be bound to each other; $R^{6'}$ and $R^{7'}$ each independently represents an hydrogen atom, halogen atom, hydroxyl group, oxygen atom, $C_{1-8}$ alkyl group, $C_{1-5}$ alkoxy group, or $C_{5-8}$ aryl group, and may be bound to each other; X represents a sulfur atom or oxygen atom; p represents 1 or 2, necessary to make the electric charge of the whole molecule 0.

3. A method of treating trypanosomiasis comprising administering an effective amount of an anti-trypanosomiasis agent comprising a compound of the following formula (3) as an active ingredient

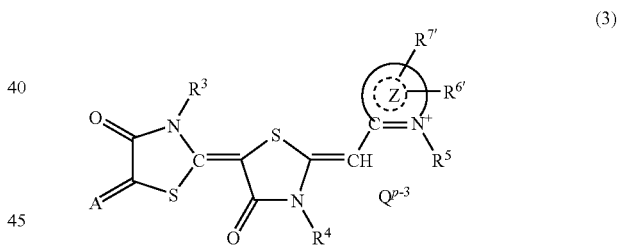

(3)

wherein $R^3$, $R^4$, and $R^5$ each independently represents a $C_{1-5}$ alkyl group or $C_{5-8}$ aryl group; $R^{6'}$ and $R^{7'}$ each independently represents an hydrogen atom, halogen atom, hydroxyl group, oxygen atom, $C_{1-8}$ alkyl group, $C_{1-5}$ alkoxy group, or $C_{5-8}$ aryl group, and may be bound to each other; Z represents a 5- or 6-membered heterocycle together with a nitrogen atom, in which hetero atoms included in the heterocycle include a nitrogen atom, oxygen atom, sulfur atom, selenium atom, tellurium atom, silicon atom, and phosphorus atom; A represents a 5- or 6-membered heterocycle, or a polycyclic ring system made from 1 or more 3- to 8-membered rings fused thereto; Q represents a physiologically acceptable anion; p represents 1 or 2, necessary to make the electric charge of the whole molecule 0.

4. The method of treating trypanosomiasis comprising administering the anti-trypanosomiasis agent according to claim 1 or 2, wherein Q represents a halogen ion, sulphonate ion, or carboxylate ion.

* * * * *